US008826726B2

(12) United States Patent
Schmid et al.

(10) Patent No.: US 8,826,726 B2
(45) Date of Patent: Sep. 9, 2014

(54) GAS SENSOR

(75) Inventors: Andreas K. Schmid, Berkeley, CA (US); Arantzazu Mascaraque, Madrid (ES); Benito Santos, Madrid (ES); Juan de la Figuera, Colmenar Viejo (ES)

(73) Assignee: The Regents of the University of California, Oakland, CA (US)

( * ) Notice: Subject to any disclaimer, the term of this patent is extended or adjusted under 35 U.S.C. 154(b) by 356 days.

(21) Appl. No.: 13/318,522

(22) PCT Filed: Apr. 29, 2010

(86) PCT No.: PCT/US2010/032990
§ 371 (c)(1),
(2), (4) Date: Feb. 6, 2012

(87) PCT Pub. No.: WO2010/129390
PCT Pub. Date: Nov. 11, 2010

(65) Prior Publication Data
US 2012/0131988 A1    May 31, 2012

Related U.S. Application Data

(60) Provisional application No. 61/175,367, filed on May 4, 2009.

(51) Int. Cl.
*G01R 33/00* (2006.01)
*G01N 27/72* (2006.01)
*G01N 27/74* (2006.01)

(52) U.S. Cl.
CPC ...................................... *G01N 27/74* (2013.01)
USPC ............ 73/31.05; 257/E43.005; 257/E43.006

(58) Field of Classification Search
USPC ....................... 73/31.05, 25.02; 257/E43.004, 257/E43.005, E43.006
See application file for complete search history.

(56) References Cited

U.S. PATENT DOCUMENTS

| | | | |
|---|---|---|---|
| 6,752,023 | B1 | 6/2004 | Meyendorf et al. |
| 2005/0009211 | A1 | 1/2005 | Linn et al. |
| 2005/0281081 | A1 | 12/2005 | Fullerton et al. |
| 2006/0240992 | A1* | 10/2006 | Brandt et al. ................ 505/844 |

(Continued)

OTHER PUBLICATIONS

Sander et al., "Reversible H-Induced Switching of the Magnetic Easy Axis in Ni/Cu(001) Thin Films," Phys Rev Lett. Dec. 10, 2004, vol. 93, Issue 24, pp. 247203-1 to 2472013-4.*

(Continued)

*Primary Examiner* — Lisa Caputo
*Assistant Examiner* — Punam Roy
(74) *Attorney, Agent, or Firm* — Lawrence Berkeley National Laboratory

(57) ABSTRACT

A gas sensor is described which incorporates a sensor stack comprising a first film layer of a ferromagnetic material, a spacer layer, and a second film layer of the ferromagnetic material. The first film layer is fabricated so that it exhibits a dependence of its magnetic anisotropy direction on the presence of a gas, That is, the orientation of the easy axis of magnetization will flip from out-of-plane to in-plane when the gas to be detected is present in sufficient concentration. By monitoring the change in resistance of the sensor stack when the orientation of the first layer's magnetization changes, and correlating that change with temperature one can determine both the identity and relative concentration of the detected gas. In one embodiment the stack sensor comprises a top ferromagnetic layer two mono layers thick of cobalt deposited upon a spacer layer of ruthenium, which in turn has a second layer of cobalt disposed on its other side, this second cobalt layer in contact with a programmable heater chip.

19 Claims, 10 Drawing Sheets

(56) References Cited

U.S. PATENT DOCUMENTS

| | | |
|---|---|---|
| 2006/0260674 A1 | 11/2006 | Tran |
| 2008/0037182 A1 | 2/2008 | Albrecht et al. |
| 2008/0084205 A1 | 4/2008 | Zimmer |
| 2008/0128285 A1 | 6/2008 | Moon et al. |

OTHER PUBLICATIONS

El Gabaly et al., "Structure and morphology of ultrathin Co/Ru(0001) films," New J Phys 9, 80 (2007).

F. El Gabaly, S. Gallego, C. Muñoz, L. Szunyogh, P. Weinberger, C. Klein, A. K. Schmid, K. F. McCarty, and J. de la Figuera, Phys. Rev. Lett. 96, 147202 (2006), "Imaging spin-reorientation transitions in consecutive atomic Co layers on Ru (0001)".

B. Santos, S. Gallego, A. Mascaraque, K. F. McCarty, A. Quesada, A. T. N'Diaye, A. K. Schmid, and J. de la Figuera, Phys. Rev. B 85 134409 (2012), "Hydrogen-induced reversible spin-reorientation transition and magnetic stripe domain phase n bilayer Co on Ru(0001)".

\* cited by examiner

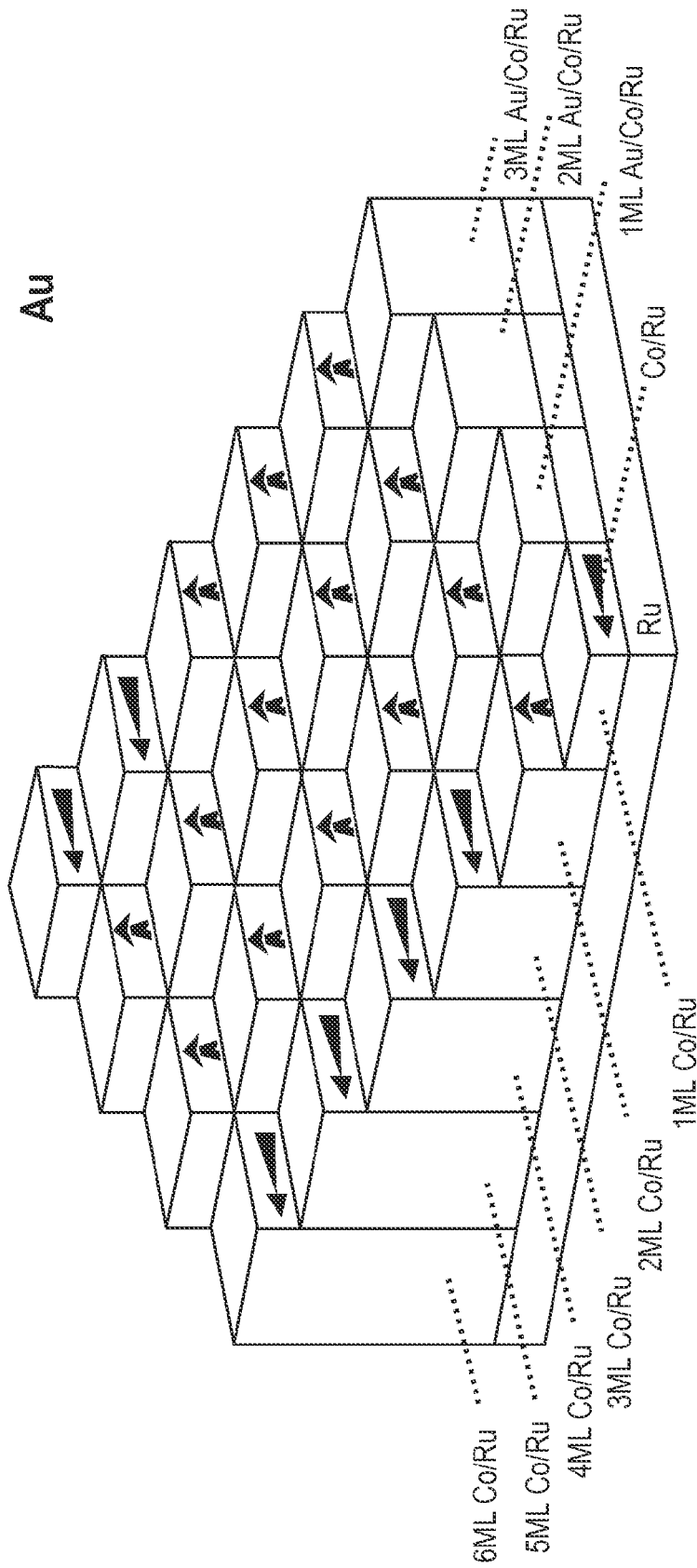
FIG. 7A/I

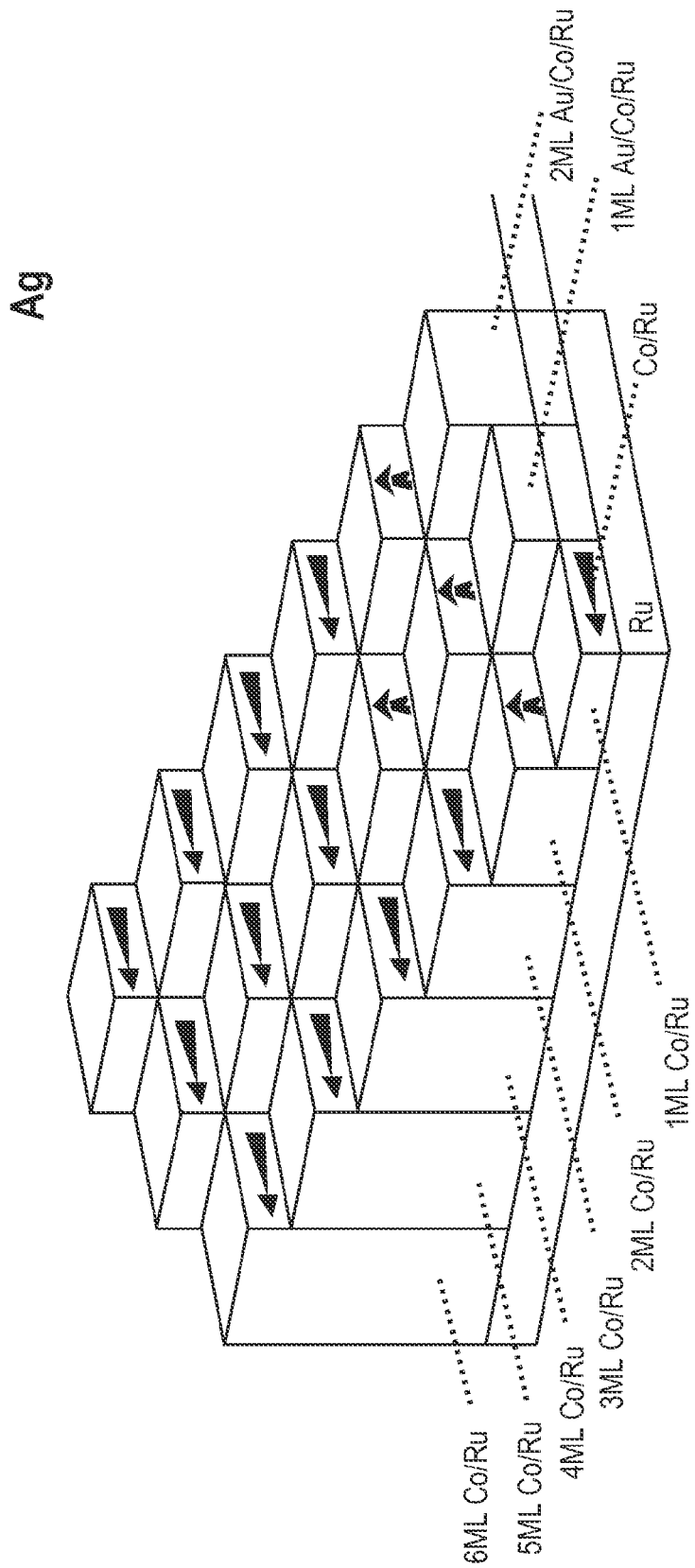
FIG. 7A/II
F. El Gabaly, et al., New Journal Of Physics 10, 073024 (2008)

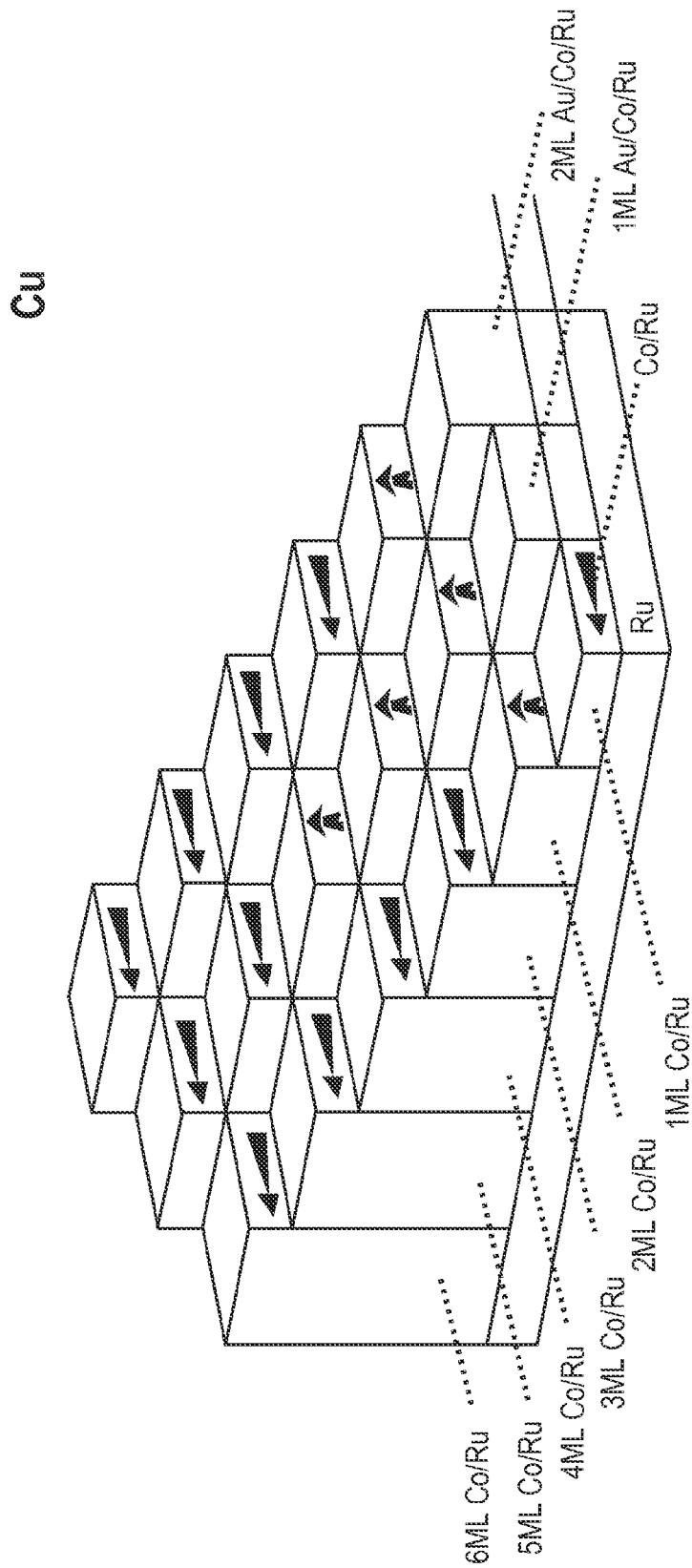
FIG. 7A/III
F. El Gabaly, et al., New Journal Of Physics 10, 073024 (2008)

Table 1. Measured easy-axis of magnetization for the different Co film/capping layer combinations studied.

| Cobalt thickness | none | 1ML Ag | 2ML Ag | 1ML Cu | 2ML Cu | 1ML Au | 2ML Au | 3ML Au |
|---|---|---|---|---|---|---|---|---|
| 2 ML | Out-of plane | Out-of plane | Out-of plane | Out-of plane | Out-of plane | Out-of plane | Out-of plane | Out-of plane |
| 3 ML | In-plane | Out-of plane | In-plane | Out-of plane | In-plane | Out-of plane | Out-of plane | Out-of plane |
| 4 ML | In-plane | In-plane | In-plane | Out-of plane | In-plane | Out-of plane | Out-of plane | Out-of plane |
| 5 ML | In-plane | In-plane | In-plane | In-plane | In-plane | Out-of plane | Out-of plane | In-plane |
| 6 ML | In-plane | In-plane | In-plane | In-plane | In-plane | Out-of plane | Out-of plane | In-plane |

FIG. 7B

GAS SENSOR

CROSS REFERENCE TO RELATED APPLICATIONS

This application claims priority to PCT application PCT/US2010/032990, filed Apr. 29, 2010, which claims priority to U.S. Provisional Application Ser. No. 61/175,367 filed May 4, 2009, entitled Gas Sensor, Andreas K. Schmid, et al. inventors, the contents of which provisional application is incorporated herein as if fully set out in its entirety.

STATEMENT OF GOVERNMENTAL SUPPORT

The invention described and claimed herein was made in part utilizing funds supplied by the U.S. Department of Energy under Contract No. DE-AC02-05CH11231. The government has certain rights in this invention.

BACKGROUND OF THE INVENTION

1. Field of the Invention

This invention relates generally to gas sensors, and more specifically to miniaturized sensors for the detection of very low levels of ambient gases, especially hydrogen.

2. Background Prior Art

There are analytical tools today which are capable of qualitatively and quantitatively detecting very small amounts of gases. These include relatively expensive and large laboratory tools with sensitivity for spectroscopic analysis of a broad range of gas compositions (example: the quadrupole mass spectrometer), as well as miniaturized sensors that are optimized for the detection of the concentration of a particular type of gas molecule (example: an oxygen sensor in automobile emission control systems).

There are needs in the field to be able to detect the presence of very small amounts of specific gases. These needs include the detection of explosive or otherwise hazardous gases, such as in factories where industrial processes are required which use or produce hazardous chemicals. Also product quality control requires engineered feedback systems to regulate process parameters on the basis of detected gases. One ubiquitous example is the emissions control system that regulates operating parameters of automobile engines as a function of the concentration of oxygen gas that is detected in the exhaust via an oxygen sensor. In the home, where natural gas is used for heating, cooking, and the like, the need for gas sensors exist to prevent explosion hazards (from gas leaks) as well as to prevent buildup of toxic emissions such as carbon-monoxide gas.

The need for gas detection sensors that are simpler, less costly to produce, more compact, and consume less power, is ongoing. For example, availability of inexpensive and compact sensors for carbon-monoxide and natural gas would make the integration of warning systems into domestic heater thermostats possible, resulting in important public heath benefits. Similar benefits would result from integration of hazardous gas monitoring technology as a standard feature in consumer products such as cellular telephones. The role of hydrogen as a fuel to replace diminishing fossil fuels generates needs for hydrogen sensors in control- and warning systems.

It was recently reported that at least for hydrogen gas, certain materials undergo a change in their easy axis of magnetization as a function of the presence or absence of hydrogen, which property has been suggested could be useful for magnetization switches. See Physical Review Letters 93, 247203 (2004). Therein, a reversible switching of the easy axis of magnetization for Ni on Cu (001) from in-plane to out-of-plane was demonstrated, by changing the partial pressure of hydrogen in the gas phase around the sample. As used herein, the term "easy axis" refers to the energetically favorable direction of the spontaneous magnetization in ferromagnetic material.

SUMMARY OF THE INVENTION

Applicants have discovered other ferromagnetic materials that in certain configurations can undergo easy axis switching in the presence of gases such as hydrogen, and have invented a sensor which takes advantage of this property. More particularly, in epitaxial cobalt films of two atomic-monolayer thicknesses grown on the [0001]-oriented surface of ruthenium crystals the easy axis of magnetization changes as a function of presence or absence of hydrogen. In the absence of hydrogen, the easy axis of magnetization of these films is perpendicular to the film plane (out-of-plane), and upon adsorption of a quantity of hydrogen the easy magnetization axis flips to lie in the plane of the film.

Based upon these observations, Applicants have developed a gas sensor in which the resistance of a multilayered sensor stack is monitored, the resistance a function of whether of not the easy axis of the exposed layer of epitaxial cobalt film is in-plane or out-of-plane, and the measured change in resistance indicative of the presence or absence of hydrogen. In one embodiment, the sensor structure is combined with a heating element, so as to effect the cyclic desorption and adsorption of the gas (e.g. hydrogen) to be detected, thus allowing for repeated, sequential measurements. In another embodiment, the rate and/or magnitude of heat cycling is modulated, the resistance of the sensor stack measured, and these measurements used to compute gas concentrations. In yet another embodiment the heater temperature modulation can be conducted at one temperature range, and then conducted at another temperature range, while continuously measuring sensor stack resistance, these measurements used to detect the presence of one, or more than one different gases.

In another embodiment, the sensor stack comprises an exposed layer of a ferromagnetic material deposited on a ruthenium layer, which in turn includes a second layer of ferromagnetic material adjacent to the back/bottom side of the ruthenium layer, this sensor stack mounted to a heater chip. In one embodiment, an anti-ferromagnetic layer is interposed between the bottom ferromagnetic layer and the heater chip. This combined sensor structure can be incorporated into a circuit board for reading out composition and concentration of the detected gases. In one embodiment, the circuit board includes a programmable heater power source, a resistance measurement circuit, and a process control unit which can be use to both calculate amounts and concentrations of the detected gases as well as, in combination with the programmable heater power source, identify the gas detected. Still further, the circuit board can be linked to an alarm, display, wireless transmitter, or other unit depending upon the intended use of the device.

BRIEF DESCRIPTION OF THE DRAWINGS

The foregoing aspects of this invention and others will be readily appreciated by the skilled artisan from the detailed description of the invention when read in conjunction with the accompanying drawings.

FIGS. 7A/I, 7A/II and FIG. 7A/III are schematic diagrams illustrating the effect the number of mono-layers of Cobalt film deposited upon a ruthenium substrate has upon the magnetic orientation of the top-most mono-layers. Also illustrated is the effect the presence of a capping layer such as gold can have on the magnetic orientation of the cobalt monolayers below. FIG. 7B presents the data of FIG. 7A I-III in tabular form.

DETAILED DESCRIPTION

In a first embodiment, a sensor-structure is constructed by fabricating a multilayer stack. The multilayer stack is made by deposition of a lower and an upper layer of ferromagnetic metal, separated by a ruthenium layer, the upper ferromagnetic layer in one embodiment being made of cobalt. This multilayer structure exhibits a giant magneto resistive effect as described in the textbook *Giant Magneto-Resistance Devices*, Springer Series in Surface Sciences, Vol. 40, Hirota, E., Sakakima, H., Inomata, K., 2002, IX, ISBN: 978-3-540-41819-1. That is, electrical resistance of the multilayer structure is low or high when the magnetization directions of the upper and the lower magnetic layers are parallel or at an angle, respectively. The lower magnetic layer is fabricated in such a manner (e.g. multiple mono layers) that its magnetization direction remains the same, while the upper layer is fabricated in such a manner (as will be subsequently explained) that its magnetization direction can flip from out-of-plane to in-plane in the presence of a gas.

Figure 1:
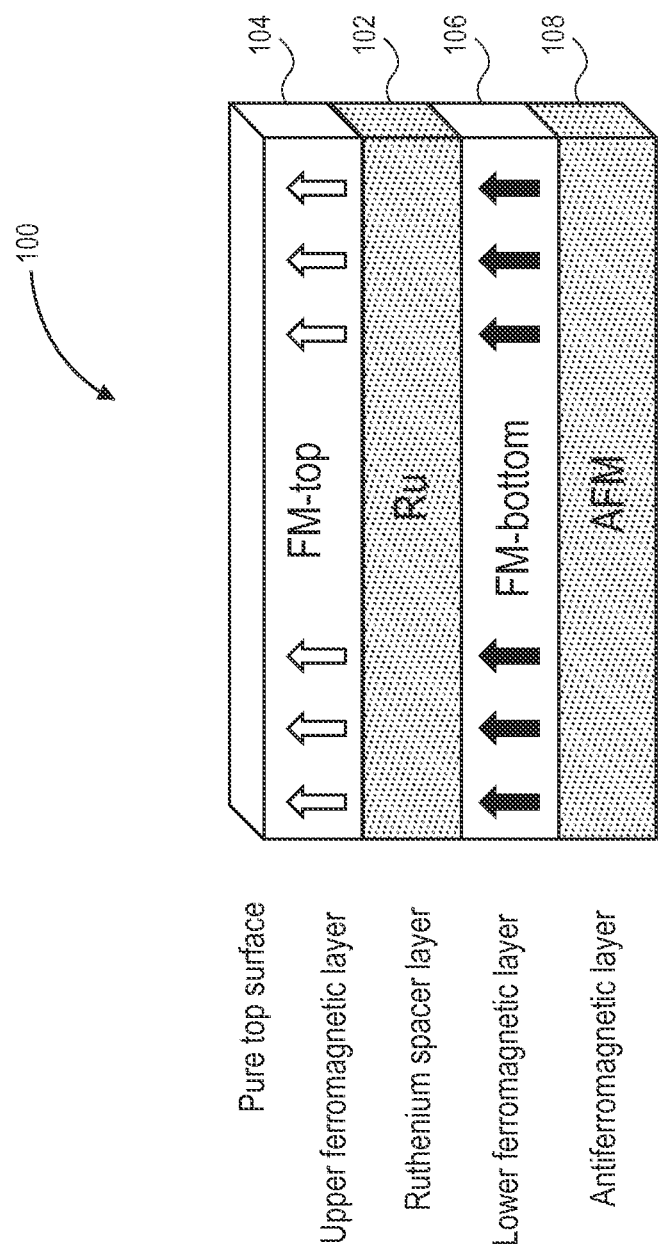
FIG. 1 is a schematic of a sensor stack according to an embodiment of the invention, in which the easy axis of both the bottom and top ferromagnetic layers are oriented in the same direction.

FIG. 1 illustrates a multi layer sensor stack 100 for gas-sensor application. A crystalline ruthenium spacer layer 102, in [0001] normal orientation, separates the epitaxial upper ferromagnetic layer 104 from the lower ferromagnetic layer 106. The lower ferromagnetic layer 106 can in turn be mounted to an antiferromagnetic layer 108 in order to use exchange biasing phenomena to stabilize the magnetization of the lower magnetic layer in a fixed magnetization direction. The actual orientation of the magnetization of this layer is not critical. That is, it can be either in-plane or out-of-plane. What is important, however, is that it remains fixed once fabrication of the sensor stack has been completed. The lower ferromagnetic layer 106 can be made of materials or structures with in-plane magnetic anisotropy (for example, cobalt films with thickness greater than a few nanometers) or it can be made of materials or structures with out-of-plane magnetic anisotropy (for example platinum-cobalt multilayers). In the embodiment illustrated in FIG. 1, a lower ferromagnetic layer with out-of plane magnetization is used (solid black arrows symbolize the magnetization direction).

The upper ferromagnetic layer is made of cobalt and has a thickness of at least two atomic mono layers (ML). The configuration is chosen such that the magnetization axis of the upper ferromagnetic layer is out-of-plane, as indicated by open arrows. Due to a "giant magnetoresistance" effect, the electrical resistance of this multilayer structure is relatively low in the condition shown in this figure, when magnetization directions in the two ferromagnetic layers are parallel.

The number of cobalt mono layers can be subject to some variation, as will be explained in greater detail in connection with a discussion of FIG. 7. Applicants' have found, however, that for a single monolayer of cobalt deposited atop a ruthenium layer, the easy axis of magnetic orientation is in-plane. When a second monolayer of cobalt is added, the easy axis flips to the perpendicular, out-of-plane orientation. Depositing a third or more mono layers of cobalt results in the easy axis flipping back to an in-plane orientation. However, by placement of a capping layer atop the third or more cobalt layer, an out-of-plane axis of magnetization can again be achieved.

When the magnetization axes of the two ferromagnetic (FM) layers are orthogonal, one to the other, the resistance increases, to a "high" condition. Depending upon the orientation of the lower FM layer, at the outset, when the top sensor layer is gas free (i.e. is free of adsorbed gas), the resistance of the stack will read "low" if the initial orientation of the lower FM layer is as shown in FIG. 1, or "high" in the case where the magnetization axis of the lower FM layer is instead in-plane (not shown).

Figure 2:
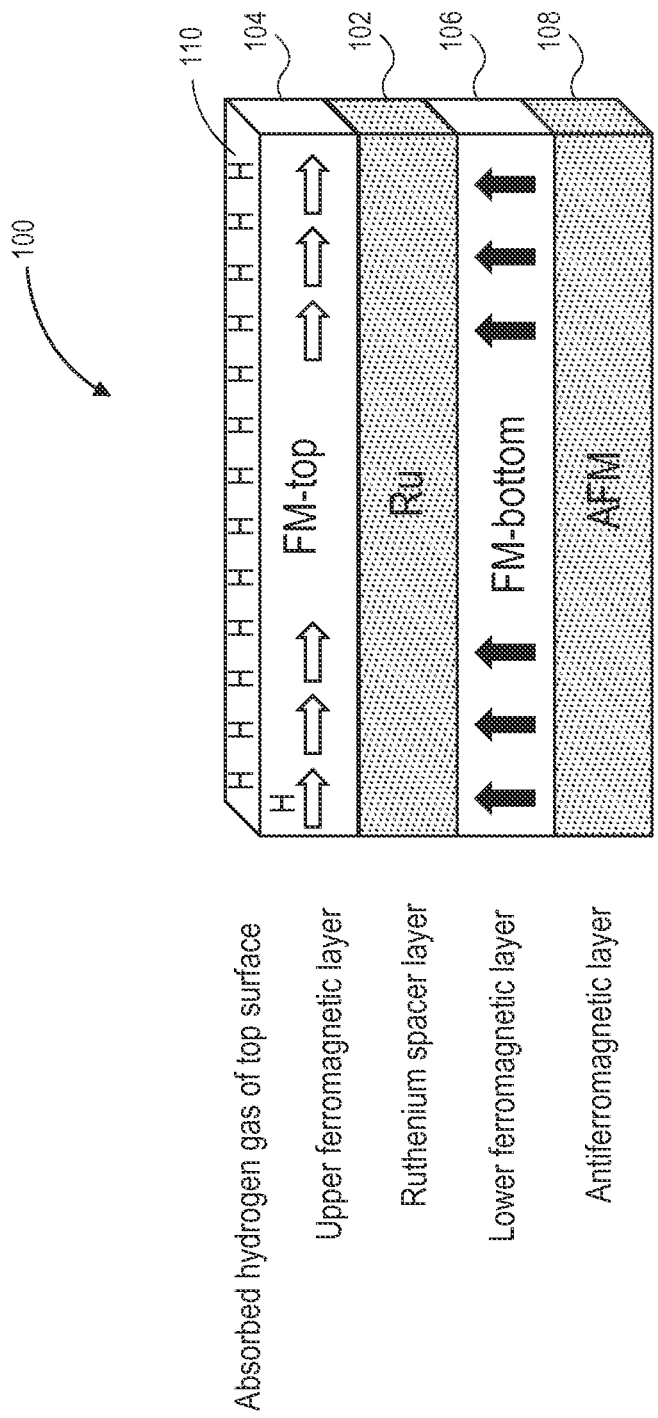
FIG. 2 is a schematic of the sensor stack of FIG. 1, wherein a gas (H) has been adsorbed onto the top layer of the ferromagnetic material, wherein the easy axis of the top layer has been flipped 90 degrees from out-of-plane to in-plane.

With reference to FIG. 2, adsorption of a gas such as hydrogen onto the surface of the upper ferromagnetic layer causes the easy axis of magnetization to flip into the in-plane direction, as indicated by the open arrows. In particular the ruthenium layer is crystalline and has normal orientation, and the upper magnetic layer is an epitaxial cobalt film with thickness of two atomic monolayers. In this form the cobalt layer exhibits an easy axis of magnetization which is out-of-plane. When the lower layer is fabricated such that its magnetization direction is also out-of-plane, then the composite exhibits a certain amount of electrical resistance. When a gas such as hydrogen 110 is adsorbed onto the surface of the upper ferromagnetic layer, then the easy axis of magnetization flips to in-plane. When the direction of the magnetization of the upper layer flips so that it is within the film plane, then the resistance of the multilayer stack goes "high", and this change can be detected electronically.

Optionally, multilayer sensor structures can be fabricated so that the lower ferromagnetic layer has an in-plane easy axis of magnetization. As with the previously described embodiment, changes of the orientation of the axis of magnetization of the upper ferromagnetic layer results in detectable changes in the electrical resistance of the multilayer sensor structure. In general, the resistance of these types of structures is lowest when the magnetization of both ferromagnetic layers point in exactly the same direction. The resistance increases as a function of the relative angle between the magnetization directions of the two ferromagnetic layers, with maximum resistance occurring when magnetization axes of the two layers are anti-aligned. Thus, as illustrated in FIG. 2, the high resistive condition indicates the presence of hydrogen, and the low resistive condition indicates its absence.

Mounting the multilayer structure on top of a heater chip permits application of programmed temperature cycles to enhance pressure range sensitivity and selectivity for the detection of various gases and mixed atmospheres. Addition of capping layers in combination with modifying the thickness of the upper ferromagnetic layer can further expand the compatibility of the gas sensor with various atmospheres, and modifies the specificity and sensitivity of the sensor.

Figure 3:
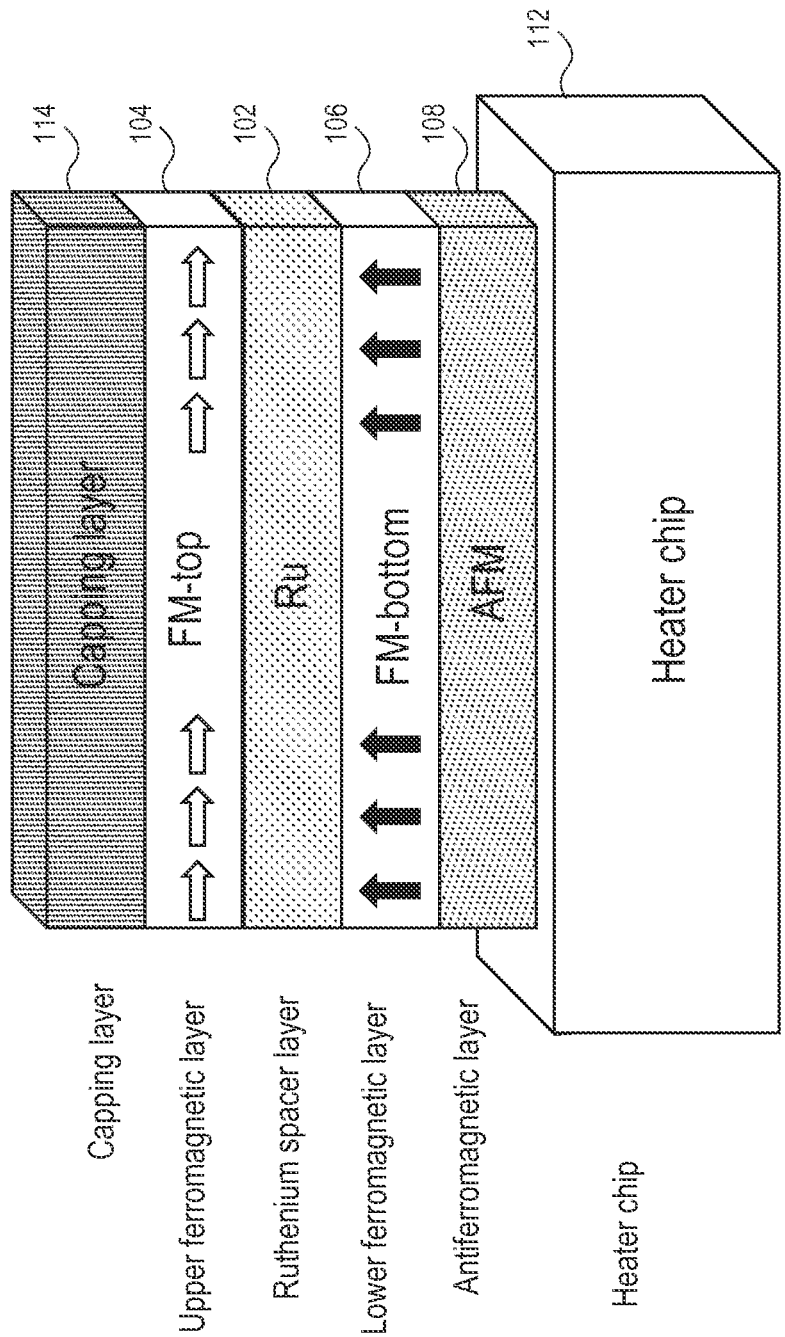
FIG. 3 is a schematic of the sensor stack of FIG. 2 including a sensor heater chip and capping layer.

More particularly, in FIG. 3, sensor stack 100 is combined with a heater 112. The heater is used to thermally desorb gases which have been adsorbed onto the surface of the detector, and the desorption temperature is a function of the chemical composition of the gas. The phenomena of adsorption and desorption are well known to those familiar with the art, as described in the textbook *Spectroscopy in Catalysis: an Introduction*, J. W. Niemantsverdriet, Edition: 2, Wiley-VCH, 2000, ISBN 352730200X, 9783527302000. In one embodiment, the heater can be a micro-chip such as sold by Protochips, Inc. of Raleigh, N.C., which can be electronically controlled to provide heat to the multilayer sensor structure in order to desorb any gas that may have been adsorbed. The temperature to which the chip is heated and the rate of temperature cycling can be regulated by programmable controlling of the heater power source. It is to be appreciated that other heater chips can be employed. The important functional criteria is that it be of small size, capable of quickly cycling, and able to heat the sensor stack to the temperatures necessary to cause gas desorption. For example, the desorption peak of hydrogen from a cobalt surface of similar nature is known to be centered about a temperature of approximately 130° C., while the desorption peak of carbon-monoxide gas from the same surface is centered at a temperature that is higher [B. G. Johnson, et al., Surf. Sci. 217, p 13-37, 1989]. For sensing the presence of a particular type of gas, the heater can be electronically controlled so that the temperature of the sensor oscillates between values T1 and T2 where T1 is below the desorption peak and T2 is above the desorption peak of the particular gas of interest.

The sensor stack may also include a capping layer 114, applied as a protective layer, such as in the case of gold. This is particularly useful where the sensor surface will be exposed to corrosive or reactive chemical gas environments. The capping layer is also used to functionalize the sensor, beyond sensitivity towards hydrogen gas, for a large range of different gases. The addition of a capping layer expands the application field of this invention by making the sensor sensitive to other types of gases. One may use gold as a capping layer, in order to suppress the adsorption, for example, of hydrogen gas, while simultaneously creating favorable conditions for the adsorption of other gases, such as methane-thiol or other thiols. The capping layer, in the case of such metals as gold, silver and/or copper can be used as a means for adjusting the direction of magnetization of the top ferromagnetic layer. To functionalize the sensor for specific gas-sensing applications, one would select the thickness of the upper ferromagnetic layer and the chemical nature and the thickness of the capping layer in such a way that sensitivity is optimized. A method for optimizing sensitivity will be hereinafter explained in connection with FIG. 7a I-III and 7b.

Figure 4:
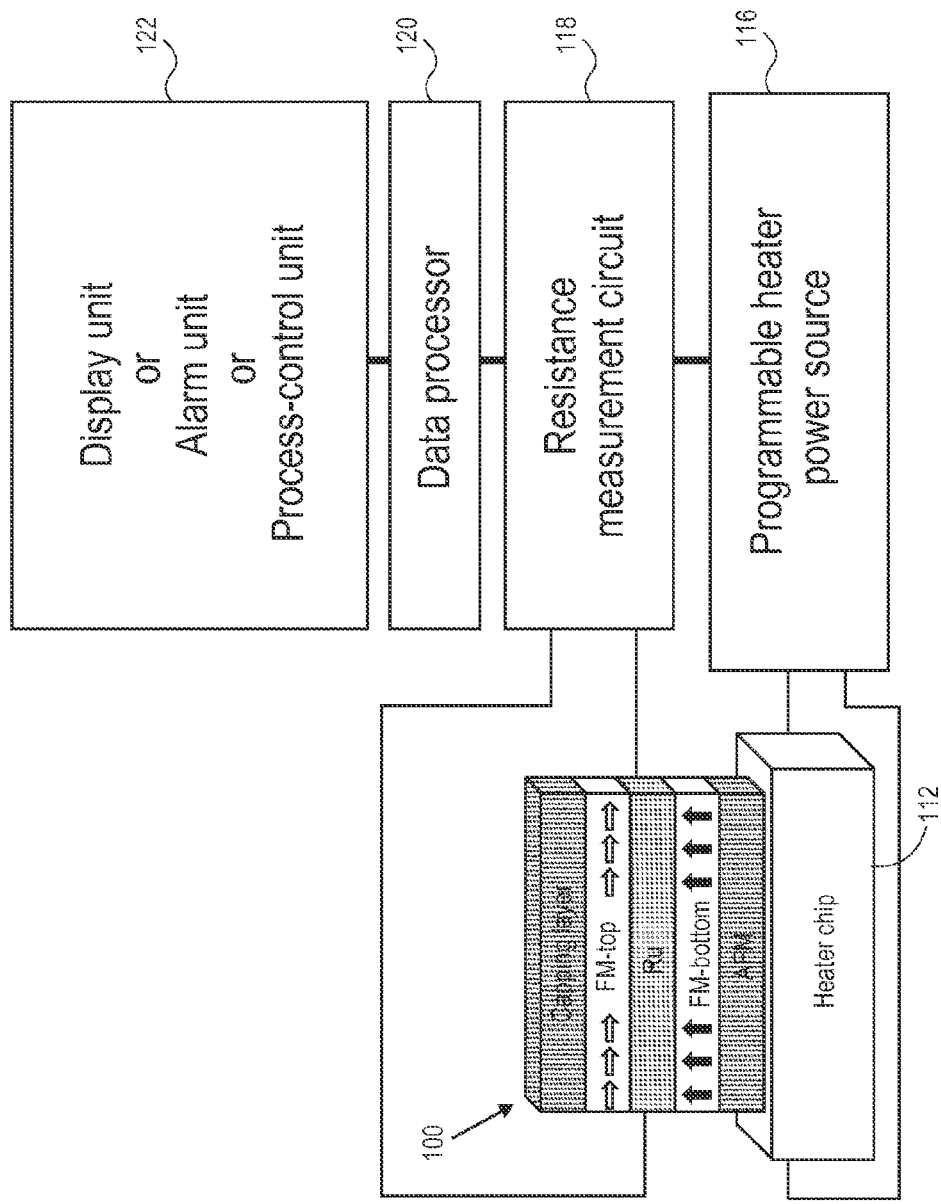
FIG. 4 a schematic of the sensor of this invention combined with sensor electronics.

FIG. 4 is a schematic illustrating the integration of the multilayer structure 100 and heater chip 112 with a programmable power source 116 and resistance measurement circuit 118. Measurement results from the system can be converted into gas composition and concentration numbers using a data processor 120, which may be a computer, a microprocessor, or microcontroller, and the output from processor 120 can be sent to a display unit, can be used as input signal for alarm systems, can be sent via wireless transmission to a remote receiver, or can be sent to a process control device 122.

In the sensor's ground (or null) state at ambient temperatures and pressures, gases will adsorb to the surface of the top cobalt monolayer, resulting in the easy axis of magnetization being in-plane. For gas detection, the heater chip is activated and the sensor stack brought to a temperature sufficient to cause gas desorption. In the illustrated embodiment for the two cobalt monolayer stack, once the sensor surface is clean, that is gas free, the easy axis of magnetization will flip 90 degrees to the out-of-plane condition. As gas begins to re-adsorb onto the top cobalt layer (or capping layer above the cobalt layer), the easy axis of magnetization will return to its in-plane orientation, the point at which the change occurs signaled by the change in sensor stack resistance.

By controlling the temperature of the stack and varying heat cycle frequency and temperature, one can both qualitatively and quantitatively determine the composition of certain gases present in the ambient atmosphere in contact with the sensor. Thus, one is able to utilize the kinetic properties of gas adsorption/desorption processes to make quantitative measurements of gas pressure. The application of variable-frequency temperature oscillations, the upper curve of FIG. 5, results in resistance oscillations of the multilayer structure. At higher gas pressures, the resistance oscillations persist to relatively high frequency temperature oscillations (middle curve). At lower gas pressures, resistance oscillations occur only at lower temperature oscillation frequencies (lower curve).

Figure 5:
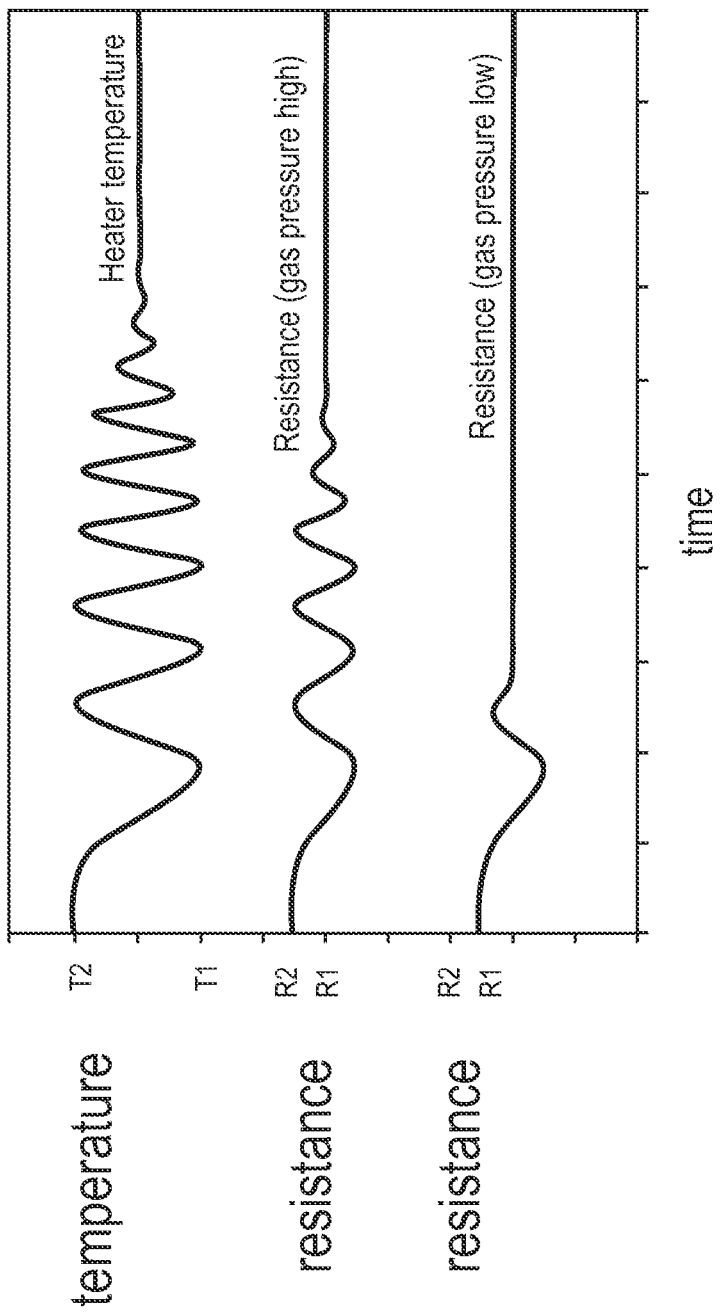
FIG. 5 is a plot of hypothetical resistance data vs. time at temperatures between T1 and T2.

In the depicted embodiment of FIG. 5, the temperature of the heater is programmed to oscillate between the values T1 and T2, where T1 is chosen to be below the desorption temperature of the gas and T2 is chosen to be above the desorption temperature of the gas. During the low-temperature phase of a cycle, gas can adsorb onto the surface of the upper ferromagnetic layer. When a sufficient amount of gas has been adsorbed, the magnetization of the upper layer flips into the film plane, resulting in a detected resistance change. During the high-temperature phase of a cycle, gas desorbs and the sensor surface becomes clean of gas, resulting in out-of plane easy axis magnetization of the upper magnetic layer, reversing the detected resistance change. Thus, in the presence of sufficient partial pressure of the gas to be detected, the resistance of the multilayer structure is observed to oscillate as a function of the programmed temperature oscillations, as shown. In the absence of sufficient amounts of the detected gas, the resistance of the multilayer structure is observed to remain at a fixed value.

The amount of time required to complete desorption of the gas from the surface of the multilayer structure can be very short, as it is a function of the value of the temperature T2 during the high-temperature phase of the cycle.

By way of programmed reduction of heater power the sensor is cooled down to the temperature T1. It should be noted that, by virtue of the miniaturized dimensions of the sensor, heating- and cooling rates can be extremely fast: using a miniaturized heater such as the type of device manufactured by Protochip, heating and cooling rates as high as 1,000,000 Celsius-per-second are possible. Consequently, the useful bandwidth of temperature oscillation frequency can range from zero to beyond kilohertz. Standard signal processing technology capable of operating in this frequency range is commercially available for the purpose of controlling heating power as well as for the purpose of monitoring sensor resistance and for the purpose of interpreting the detected resistance changes in terms of gas pressure. (Existing technology used in consumer products such as personal music players exploits a related magnetoresistance phenomenon as the preferred method to read data from magnetic data storage media. In these types of products, signal-processing speed exceeds by a large factor the processing speed used for this gas-sensor invention).

Once the temperature of the sensor is close to T1 (below the desorption temperature of the gas), the amount of time required to adsorb the sufficient quantity of gas to cause flipping of the upper layer's easy axis of magnetization to in-plane orientation is a function of the partial pressure of the detected gas. These phenomena are used for quantitative measurement of gas concentration. In one embodiment, the heater is programmed to oscillate temperature of the multilayer structure between the values T1 and T2 at variable frequency, for example in form of a chirped harmonic function of time as depicted in FIG. 5 and in FIG. 6. A chirped harmonic signal is a signal that oscillates with a fixed amplitude (between the values T1 and T2) at a frequency that continuously varies, starting from a minimum value of frequency and increasing towards a maximum value of frequency. In the presence of a certain amount of the detected gas, resistance of the multilayer structure is observed to oscillate as a function of low-frequency programmed temperature oscillations, while the resistance of the multilayer structure is observed to remain fixed for high-frequency temperature oscillations. The value of the frequency where resistance oscillations are quenched is a function of the pressure and thus the concentration of the detected gas.

Figure 6:
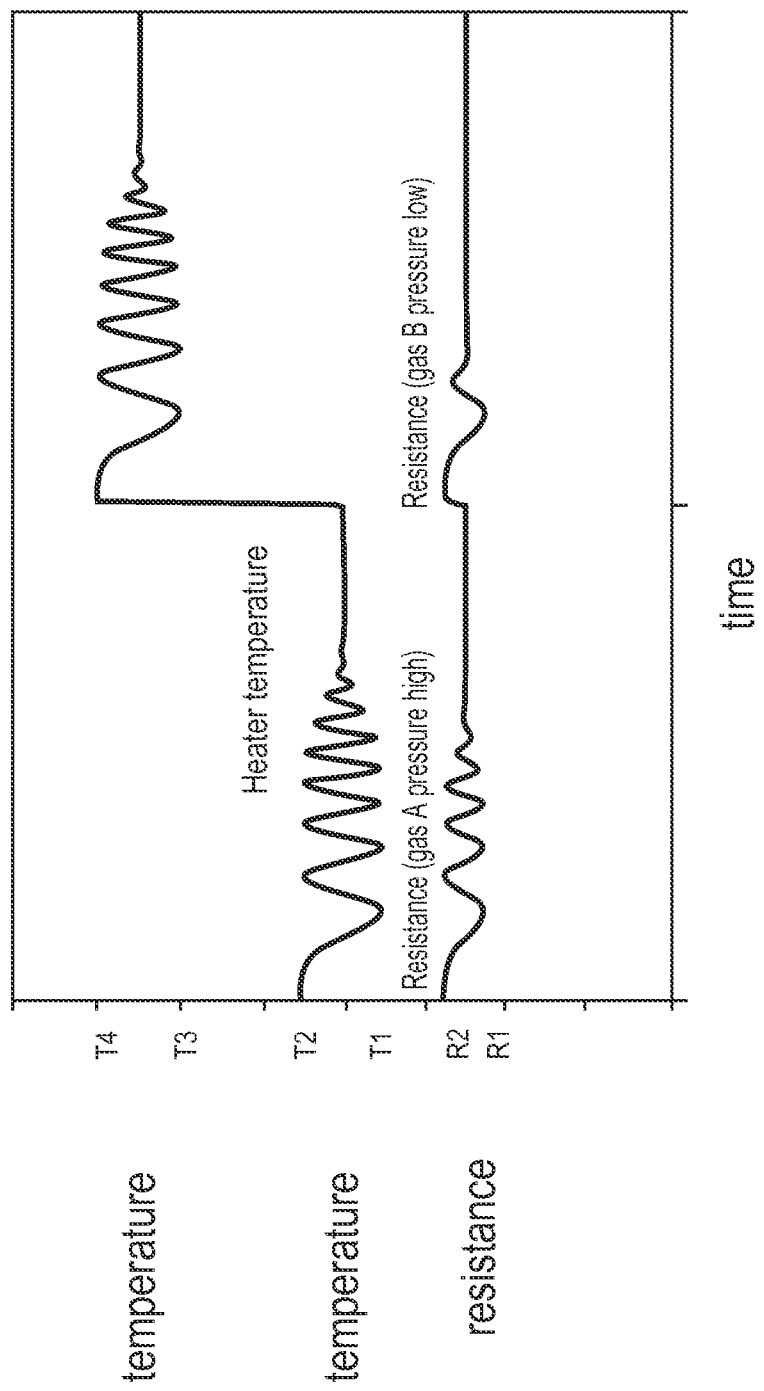
FIG. 6 is a plot of hypothetical resistance data against time at two different temperature levels.

FIG. 6 is illustrative of how the presence of several difference gases may be detected using the sensor of this invention. The binding energy of different gases adsorbed on the surface of the multilayer structure will be different. Consequently, the temperature range at which a gas of type A desorbs is different from the temperature range at which a gas of type B desorbs. One can choose temperature values T1 and T2 to be below and above the desorption temperature of gas A. Further, one can choose temperature values T3 and T4 to be below and above the desorption temperature of gas B. Further, the heater can be programmed to oscillate during a first time-interval between temperature values T1 and T2 in the form of a chirped sinusoidal function of time, and, during a second time-interval, to oscillate between temperature values T3 and T4 in the form of a chirped sinusoidal function of time. Monitoring the resistance of the multilayer structure provides a measurement of the partial pressure of gas A during the first time-interval and a measurement of the partial pressure of gas B during the second time-interval. Similarly, the sensor can be programmed for the detection of more than two types of gases.

Other temperature variation regimens can be employed, instead of chirped harmonic temperature oscillations, for gas analysis. The important point is that, (1), gases adsorb and desorb as a function of temperature and, (2), detectable resistance change of the multilayer stack result from presence or absence of an adsorbed gas layer on the surface of the sensor. Tracking sensor resistance changes as a function of chirped harmonic temperature oscillations is just one way to use the sensor for quantitative pressure measurements. Tracking the time-dependence of the resistance of the sensor during a time interval following a temperature pulse is another approach which can be used to quantify gas detection. Tracking sensor resistance changes as a function of controlled linear temperature ramps is still yet another method which could be employed to quantify gas detection, and additional other methods exist and are included in this invention.

As previously noted, it may be desirable to cap the topmost cobalt monolayer with a protective layer such as gold, especially in the case where the sensor will be exposed to harsh chemical environments such as in a chemical plant. In the case of a two mono layer thick film of cobalt over a ruthenium substrate, the application of one or more layers of gold will not affect the easy axis orientation of the top cobalt layer (i.e., it remains oriented out-of-plane). Other suitable capping materials that can be used with such a cobalt sensor stack can include copper and silver.

Applicants' have also observed in the case of multiple (i.e. more than two) layers of cobalt, the in-plane orientation of the magnetic axis can be flipped to out-of-plane by the addition of capping layers of silver or copper, as well as gold. Combinations so far explored which result in an out-of-plane orientation are illustrated in FIG. 7A, I-III and Table 1 of FIG. 7B.

The embodiment discussed herein has been described in connection with the detection of hydrogen. It is to be appreciated by one of ordinary skill in the art that the gas sensor of this invention can be used to detect other gases such as CO, $CO_2$, oxygen, methane and other alkenes, methane thiol and other thiols, methanol and other alcohols, numerous other flammable gases, and numerous other toxic gases, etc. Generally any gas which adsorbs either directly onto a ferromagnetic material, or onto a capping layer used to functionalize a ferromagnetic layer, and causes a change in the direction of the materials' easy axis of magnetization, and can be desorbed by raising the temperature of the ferromagnetic material, or the capping layer, may be detected according to the sensor of this invention.

It should also be appreciated, that while the described embodiments were limited to cobalt as the ferromagnetic material, and to gold, copper, and silver as the capping layers, other materials can be employed. What is required is that the selected combination of a non-magnetic spacer layer and an upper ferromagnetic layer and a capping layer be capable of exhibiting either perpendicular magnetic anisotropy or in-plane magnetic anisotropy, as a function of the adsorption or desorption of a gas. Such candidate ferromagnetic materials include cobalt, nickel, iron, as well as alloys, oxides, and other compounds. Likewise other materials than ruthenium can be used as the spacer layer, that is the interlayer between the top and bottom magnetic layers of the sensor stack. What matters is that a magneto resistance-effect is induced; that is, the interlayer decouples the magnetism of the upper ferromagnetic layer from the magnetism of the lower ferromagnetic layer in such a way that the electrical resistance of the entire multilayer stack is a function of the relative directions of the magnetizations in the two ferromagnetic layers. Besides ruthenium, candidate materials for the spacer layer include other metals such as platinum, palladium, copper, silver, gold, and other non-magnetic metals, as well as oxides including MgO and other compounds.

The thickness and composition of the interlayer is a design parameter that can be varied in order to optimize functional properties of the sensor: optimizing the strength of the magneto resistance effect may benefit detector readout speed and/or accuracy, while other choices of materials may increase temperature range of the sensor, thereby increasing range of sensitivity to various gases. Other interlayer material choices may be used to optimize economy or durability of the sensor.

The composition and thickness of the lower ferromagnetic layer need not necessarily be the same as that of the upper ferromagnetic layer. The lower ferromagnetic layer is designed to be "magnetically hard", that is, the direction of its magnetization is fixed and does not easily change as a function of any external environmental influences. The upper ferromagnetic layer, in combination with the capping layer, is designed to possess only a limited amount of stability, so that the direction of its magnetization may change as a function of adsorption of gas.

The sensors of this invention gas can be quite small. Miniaturization is an important advantage for several reasons, including economy of production, as well as suitability for integration of sensors into other devices (for example, integration of explosive gas or toxic gas detectors into household thermostats, cellular telephones, passenger or baggage screening equipment, etc.). Magneto resistive devices are nowadays a mature technology and micrometer-scale miniaturization is standard (for example, data-read heads in magnetic hard-disk storage devices are similarly small). One factor that determines the size of the sensor is the size of the heater chip—the Protochips heater has a size of less than 3 millimeters linear dimensions, and the size of the active heated region is on the micrometer-scale. On the basis of existing fabrication technologies, it is feasible to fabricate the sensor described in this invention in sufficiently compact size to permit integration within a standard IC package of a few millimeter linear dimensions. Sensor miniaturization also results in advantageous reduction of power consumption, which is particularly useful for applications where the sensor is integrated in battery-powered devices. In combination with the versatility to detect different types of gases, miniaturization and associated economic advantage opens up new commercial opportunities that have never been realized before. For example, hazardous gas sensing could be incorporated as a standard feature of a hand held wireless phone such as a cell-phone, or a smart phone such as iPhone®, Palm Pilot®, or Blackberry®, so that phone users would receive a warning in case the concentration of explosive or toxic gases in the environment exceeds safe levels. The smart/cell-phone could even be programmed to automatically relay to responders the detection of a hazard, nature of hazardous substance, location of hazard, etc.

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself.

We claim:

1. A gas sensor stack including:
   a first ferromagnetic layer, an orientation of an easy axis of magnetization of the first ferromagnetic layer being fixed;
   a non-magnetic layer disposed on the first ferromagnetic layer; and
   a second ferromagnetic layer disposed on the non-magnetic layer, an orientation of an easy axis of magnetization of the second ferromagnetic layer being variable, the orientation of the easy axis of magnetization of the second ferromagnetic layer being out of a plane of the second ferromagnetic layer when no gases are adsorbed over the second ferromagnetic layer.

2. The gas sensor stack of claim 1 wherein the orientation of the easy axis of magnetization of the second ferromagnetic layer at its ground state at ambient temperature and ambient atmosphere is in the plane of the second ferromagnetic layer.

3. The gas sensor stack of claim 1 further including:
   an anti-ferromagnetic layer, wherein the first ferromagnetic layer is disposed on the anti-ferromagnetic layer.

4. The gas sensor stack of claim 3 further including:
   a heater, wherein the anti-ferromagnetic layer is disposed on the heater.

5. The gas sensor stack of claim 4 further including:
   a heater power source coupled to the heater.

6. The gas sensor stack of claim 1 further including:
   a resistance measurement circuit connected to the first ferromagnetic layer and the second ferromagnetic layer and configured to measure a resistance between the first ferromagnetic layer and the second ferromagnetic layer.

7. The gas sensor stack of claim 1 wherein the second ferromagnetic layer is comprises cobalt.

8. The gas sensor stack of claim 1 wherein the second ferromagnetic layer comprises at least two monolayers of cobalt.

9. The gas sensor stack of claim 1 wherein the first ferromagnetic layer is comprises cobalt.

10. The gas sensor stack of claim 1 wherein the non-magnetic layer is comprises ruthenium.

11. The gas sensor stack of claim 1 further including:
    a capping layer disposed on the second ferromagnetic layer.

12. The gas sensor stack of claim 11 wherein the capping layer comprises one or more monolayers of gold.

13. The gas sensor stack of claim 1 wherein the second ferromagnetic layer is selected from a group consisting of cobalt, nickel, and iron.

14. The gas sensor stack of claim 1 wherein the non-magnetic layer is selected from a group consisting of platinum, palladium, copper, silver, gold, and a non-magnetic metal.

15. The gas sensor stack of claim 1 wherein the orientation of the easy axis of magnetization of the second ferromagnetic layer is dependent on a thickness of the second ferromagnetic layer.

16. A method including:
   (a) providing a gas sensor including:
      a first ferromagnetic layer, an orientation of an easy axis of magnetization of the first ferromagnetic layer being fixed,
      a non-magnetic layer disposed on the first ferromagnetic layer, and
      a second ferromagnetic layer disposed on the non-magnetic layer, an orientation of an easy axis of magnetization of the second ferromagnetic layer being variable;
   (b) exposing the gas sensor to an ambient atmosphere;
   (c) heating the second ferromagnetic layer of the gas sensor to desorb gases from the second ferromagnetic layer;
   (d) cooling the second ferromagnetic layer; and
   (e) measuring a resistance between the first ferromagnetic layer and the second ferromagnetic layer during operation (d).

17. The method of claim 16 further including:
   repeating operations (c), (d), and (e).

18. The method of claim 16 further including:
   after operation (e), determining when the resistance between the first ferromagnetic layer and the second ferromagnetic layer changes.

19. A gas sensor stack including:
   a heater;
   an anti-ferromagnetic layer disposed on the heater;
   a first ferromagnetic layer disposed on the anti-ferromagnetic layer, an orientation of an easy axis of magnetization of the first ferromagnetic layer being fixed;
   a non-magnetic layer disposed on the first ferromagnetic layer; and
   a second ferromagnetic layer disposed on the non-magnetic layer, an orientation of an easy axis of magnetization of the second ferromagnetic layer being variable, the orientation of the easy axis of magnetization of the second ferromagnetic layer being out of a plane of the second ferromagnetic layer when no gases are adsorbed over the second ferromagnetic layer.

* * * * *